(12) United States Patent
Holmqvist (10) Patent No.: US 10,967,128 B2
(45) Date of Patent: Apr. 6, 2021

(54) ADMINISTRATION MECHANISM FOR A MEDICAMENT DELIVERY DEVICE

(71) Applicant: SHL MEDICAL AG, Zug (CH)

(72) Inventor: Anders Holmqvist, Värmdö (SE)

(73) Assignee: SHL MEDICAL AG, Zug (CH)

(*) Notice: Subject to any disclaimer, the term of this patent is extended or adjusted under 35 U.S.C. 154(b) by 246 days.

(21) Appl. No.: 16/315,282

(22) PCT Filed: Jun. 27, 2017

(86) PCT No.: PCT/EP2017/065820
§ 371 (c)(1),
(2) Date: Jan. 4, 2019

(87) PCT Pub. No.: WO2018/010947
PCT Pub. Date: Jan. 18, 2018

(65) Prior Publication Data
US 2019/0240409 A1  Aug. 8, 2019

(30) Foreign Application Priority Data

Jul. 14, 2016 (EP) ..................................... 16179476

(51) Int. Cl.
*A61M 5/20* (2006.01)
*A61M 5/31* (2006.01)
*A61M 5/32* (2006.01)

(52) U.S. Cl.
CPC ............ *A61M 5/2033* (2013.01); *A61M 5/20* (2013.01); *A61M 5/3129* (2013.01);
(Continued)

(58) Field of Classification Search
CPC .... A61M 5/2033; A61M 5/20; A61M 5/3129; A61M 5/3271; A61M 2005/2006; A61M 2205/18; A61M 5/3205; A61M 5/3202
See application file for complete search history.

(56) References Cited

U.S. PATENT DOCUMENTS

2012/0010576 A1*  1/2012  Raab ................. A61M 5/31585
                                                    604/211

FOREIGN PATENT DOCUMENTS

CN       103328026 A     9/2013
TW       201433326 A     9/2014
(Continued)

OTHER PUBLICATIONS

International Search Report and Written Opinion for Int. App. No. PCT/EP2017/065820, dated Nov. 8, 2017.

*Primary Examiner* — Theodore J Stigell
*Assistant Examiner* — Rachel T. Smith
(74) *Attorney, Agent, or Firm* — McDonnell Boehnen Hulbert & Berghoff LLP (57) ABSTRACT

The present disclosure relates to an administration mechanism for a medicament delivery device having a movable sleeve, and a delivery member cover having a distal end portion configured to receive the movable sleeve. The delivery member being configured to be linearly displaceable between a first position and a second position relative to the movable sleeve, wherein the distal end portion has an end face defining a guide surface and the movable sleeve has a radially outwards extending first follower structure configured to cooperate with the guide surface when the delivery member cover is moved from the first position towards the second position, causing the movable sleeve to rotate.

19 Claims, 6 Drawing Sheets

(52) U.S. Cl.
CPC ... *A61M 5/3271* (2013.01); *A61M 2005/2006* (2013.01); *A61M 2205/18* (2013.01)

(56) References Cited

FOREIGN PATENT DOCUMENTS

| | | |
|---|---|---|
| WO | 2011/123024 A1 | 10/2011 |
| WO | 2012/003516 A2 | 1/2012 |
| WO | 2013/016832 A1 | 2/2013 |
| WO | 2014/095424 A1 | 6/2014 |
| WO | WO-2014095424 A1 * 6/2014 .......... A61M 5/3204 |
| WO | 2015/121081 A1 | 8/2015 |

* cited by examiner

ADMINISTRATION MECHANISM FOR A MEDICAMENT DELIVERY DEVICE

CROSS REFERENCE TO RELATED APPLICATIONS

The present application is a U.S. National Phase Application pursuant to 35 U.S.C. § 371 of International Application No. PCT/EP2017/065820 filed Jun. 27, 2017, which claims priority to European Patent Application No. 16179476.3 filed Jul. 14, 2016. The entire disclosure contents of these applications are herewith incorporated by reference into the present application.

TECHNICAL FIELD

The present disclosure generally relates to medical devices. In particular, it relates to an administration mechanism for a medicament delivery device and to a medicament delivery device comprising such an administration mechanism.

BACKGROUND

Medicament delivery devices such as auto-injectors are very common on the market as they facilitate for users to manage medicament administration.

An example of a medicament delivery device is disclosed in WO 2011/123024 A1. The medicament delivery device has a tubular housing and a tubular activation member, displaceable from an extended position to a retracted position relative to the housing, and configured to be returned to the extended position. The medicament delivery device also has a tubular operation member configured to cooperate with the tubular activation member. The tubular activation member has first co-acting means in the form of two oppositely arranged radially inwards extending protrusions, and the tubular operation member has second co-acting means interactively connected to the corresponding first co-acting means. In particular, the second co-acting means include grooves on the outer surface of the tubular operation member and the radial inwards extending protrusions are adapted to be guided within a respective groove, forcing the tubular operation member to rotate when the tubular activation member is axially moved from the extended position towards the retracted position. Moreover, the tubular operation member has locking means, e.g. a respective flexible tongue, in the grooves, which lock a respective one of the radially inwards extending protrusions when the tubular activation member returns from the retracted position towards the extended position and the radially inwards extending protrusions move over the respective tongue. In this manner, the tubular activation member is locked from displacement as it returns to the extended position after medicament administration.

SUMMARY

The radially inwards extending protrusions of the tubular activation member may extend radially inwards to such an extent that when the medicament container is introduced into the housing during assembly, the medicament container, in particular a distal end flange thereof, may momentarily engage with the protrusions as the medicament container is moved forward in the housing. This may damage the protrusions so that they become weakened, which may result in that the protrusions break if the medicament delivery device, with the tubular activation member being in the locked position, is dropped accidentally, and the tubular activation member absorbs the impact. This could lead to the tubular activation member being moved into the housing, towards the retracted position thereof thereby exposing the delivery member.

In view of the above, a general object of the present disclosure is to provide an administration mechanism for a medicament delivery device which solves or at least mitigates the problems of the prior art.

A first aspect of the present disclosure provides an administration mechanism for a medicament delivery device, where the administration mechanism has a movable sleeve, and a delivery member cover having a distal end portion configured to receive the movable sleeve. The delivery member is configured to be linearly displaceable between a first position and a second position, relative to the movable sleeve. The distal end portion of the delivery member has an end face defining a guide surface and the movable sleeve has a radially outwards extending first follower structure configured to cooperate with the guide surface when the delivery member cover is moved from the first position towards the second position, which in turn causes the movable sleeve to move.

The guide surface is an end surface of the delivery member cover. In particular, the guide surface extends between the outer surface of the delivery member cover and the inner surface of the delivery member cover. The guide surface hence defines the radial thickness, or wall thickness, of the delivery member cover. The guide surface, which enables rotation of the movable sleeve, will therefore not extend radially beyond the inner surface of the delivery member cover. As a result, there will be no risk of momentary engagement with a medicament container when a medicament container comprising the administration mechanism is assembled.

According to one embodiment the movable sleeve comprises a radially outwards extending second follower structure and the distal end portion of the delivery member cover has a cut-out configured to receive the radially outwards extending second follower structure, wherein the radially outwards extending second follower structure is configured to cooperate with a wall of the cut-out, causing rotation of the movable sleeve when the delivery member cover is moved from the second position towards the first position.

It may thereby be possible to detect movement of the movable sleeve both during administration, when the delivery member cover moves from the first position to the second position, and also when drug delivery has been finalised and the delivery member cover moves from the second position to the first position, due to the further rotation. It may thereby be possible to register both drug delivery and finalization thereof, for example by means of a sensor or switch configured to detect rotation of the movable sleeve.

According to one embodiment the radially outwards extending second follower structure has a triangular shape and the wall of the cut-out is a slanting surface.

According to one embodiment the movable sleeve has a lock structure configured to be received by the cut-out and configured to prevent movement of the delivery member cover when returned to the first position from the second position.

According to one embodiment the radially outwards extending first follower structure has an oblique surface configured to cooperate with the guide surface.

According to one embodiment the radially outwards extending first follower structure is a circumferentially extending rib.

According to one embodiment the movable sleeve has a lock structure and wherein the delivery member cover has a cut-out configured to receive the lock structure when the movable sleeve is rotated by the delivery member cover.

According to one embodiment the cut-out has an axially extending elongated portion configured to allow linear displacement of the delivery member cover relative to the lock structure when the lock structure is arranged in the cut-out.

According to one embodiment the lock structure is flexible radially inwards and the delivery member cover has a through-opening configured to receive the lock structure when the delivery member cover is returned from the second position to the first position.

According to one embodiment the through-opening is arranged distally from and axially aligned with the axially extending elongated portion of the cut-out.

According to one embodiment the lock structure and the through-opening form a snap lock function.

According to one embodiment the lock structure is arranged proximally relative to the radially outwards extending first follower structure.

According to one embodiment the guide surface is a cam surface.

One embodiment comprises a first resilient member configured to bias the delivery member cover towards the first position.

There is, according to a second aspect of the present disclosure provided, a medicament delivery device comprising: a housing having a proximal opening, an administration mechanism according to the first aspect, configured to be received by the housing, wherein in the first position the delivery member cover is configured to extend from the proximal opening, and wherein the delivery member cover is configured to be rotationally locked relative to the housing.

Generally, all terms used in the claims are to be interpreted according to their ordinary meaning in the technical field, unless explicitly defined otherwise herein. All references to "a/an/the element, apparatus, component, means, etc. are to be interpreted openly as referring to at least one instance of the element, apparatus, component, means, etc., unless explicitly stated otherwise.

BRIEF DESCRIPTION OF THE DRAWINGS

The specific embodiments of the inventive concept will now be described, by way of example, with reference to the accompanying drawings, in which.

DETAILED DESCRIPTION

The inventive concept will now be described more fully hereinafter with reference to the accompanying drawings, in which exemplifying embodiments are shown. The inventive concept may, however, be embodied in many different forms and should not be construed as limited to the embodiments set forth herein; rather, these embodiments are provided by way of example so that this disclosure will be thorough and complete, and will fully convey the scope of the inventive concept to those skilled in the art. Like numbers refer to like elements throughout the description.

The term "proximal end" as used herein, when used in conjunction with an administration mechanism, refers to that end of the administration mechanism which is intended to be pointed towards the injection site during medicament administration, when the administration mechanism is properly installed in a medicament delivery device. The same considerations also apply when referring to any component of the administration mechanism. The "distal end" is the opposite end relative to the proximal end. With "proximal direction" and, equivalently, "proximally" is meant a direction from the distal end towards the proximal end, along the central axis of the safety mechanism. With "distal direction" or "distally" is meant the opposite direction to "proximal direction".

The present disclosure relates to an administration mechanism comprising a movable sleeve and a delivery member cover configured to cooperate with each other such that linear movement of the delivery member cover translates to rotational movement of the movable sleeve. The delivery member cover has a distal end portion which has an end face. The end face connects the outer surface of the delivery member cover with the inner surface of the delivery member, and is hence a distal end wall of the delivery member cover. That dimension of the end face which extends from the outer surface to the inner surface is hence the thickness of the delivery member cover. The end face defines a guide surface.

The movable sleeve has a radially outwards extending first follower structure configured to cooperate with the guide surface of the delivery member cover. Moreover, the delivery member cover is movable relative to the movable sleeve, between a first position and a second position. When mounted inside the housing of a medicament delivery device, the first position corresponds to an extended position of the delivery member cover relative to the housing and the second position corresponds to a retracted position relative to the housing. When the delivery member cover is moved from the first position to the second position, the guide structure is configured to cooperate with the radially outwards extending first follower structure, causing rotation of the movable sleeve. The guide surface and the radially outwards extending first follower structure may hence be seen to have cam functionality.

Figure 1:
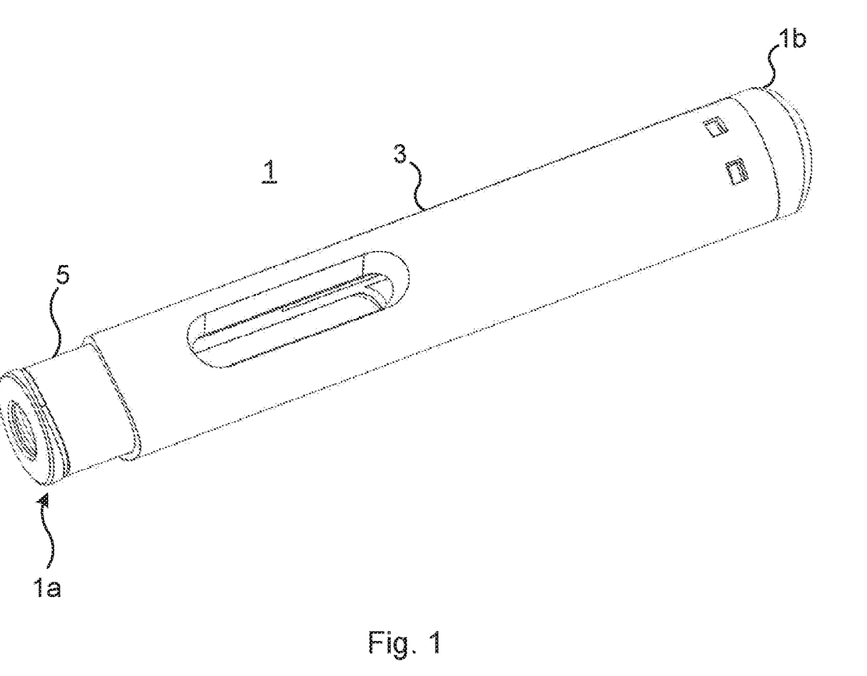
FIG. 1 is a perspective view of an example of a medicament delivery device.

FIG. 1 shows an example of a medicament delivery device 1. The exemplified medicament delivery device 1 is an injector, in particular an auto-injector. The medicament delivery device 1 has a proximal end 1a and a distal end 1b and comprises an example of an administration mechanism of the type described above.

Medicament delivery device 1 has a housing 3 and a delivery member cover 5, which in FIG. 1 is arranged in the extended position relative to the housing 3. Linear movement of the delivery member cover 5 from the extended position to the retracted position causes activation of the medicament delivery device 1.

Figure 2:
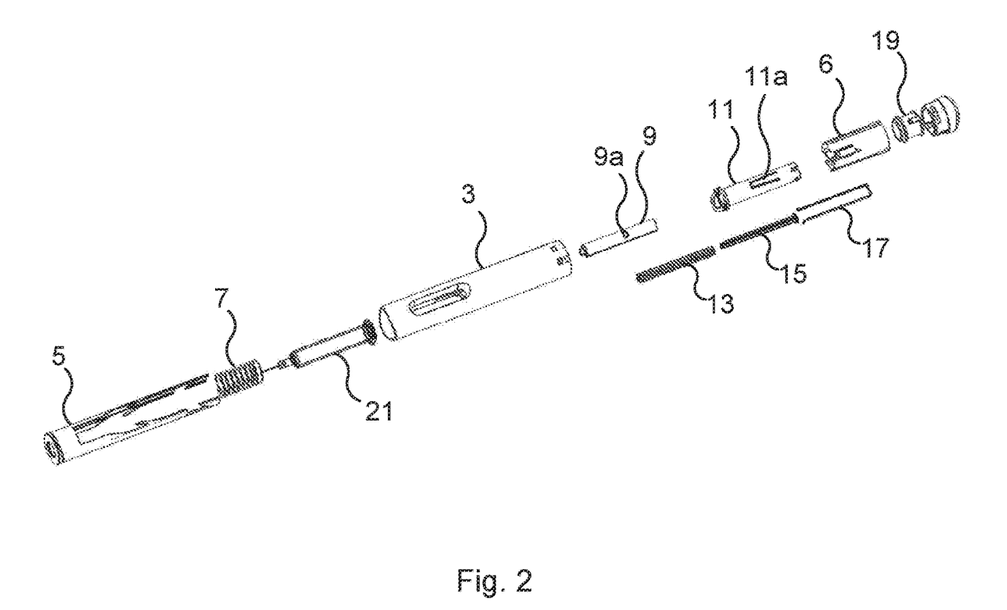
FIG. 2 shows an exploded view of the medicament delivery device in FIG. 1.

FIG. 2 shows an exploded view of the medicament delivery device 1. The exemplified medicament delivery device 1 furthermore includes a movable sleeve 6, which together with the delivery member cover 5 forms an administration mechanism. The medicament delivery device 1 also includes a first resilient member 7, a plunger rod 9, a tubular member 11, a second resilient member 13, a rod 15, a feedback member exemplified by U-bracket 17, and an end member 19.

The first resilient member 7 is configured to bias the delivery member cover 5 in the proximal direction. Hereto, the delivery member cover 5 is configured to be biased towards the extended position relative to the housing 3. The first resilient member 7 may for example be a spring.

The movable sleeve 6, or rotator, which is tubular, is configured to cooperate with the delivery member cover 5 so that linear displacement of the delivery member cover 5 causes rotation of the movable sleeve 6. Furthermore, the movable sleeve 6 is configured to receive the tubular member 11.

The tubular member 11 is configured to receive the plunger rod 9 and the U-bracket 17, which is configured to be arranged around the plunger rod 9. Furthermore, the second resilient member 13 is configured to bias the plunger rod 9 proximally.

The second resilient member 13 is configured to be arranged around the rod 15. The rod 15 hence ensures that the resilient member 13, typically a spring, maintains its axial elongation during compression and expansion. The exemplified plunger rod 9 is hollow and configured to receive the rod 15 and the second resilient member 13. The U-bracket 17 has two legs and is configured to receive the plunger rod 9 therebetween. The U-bracket 17 has a distal transverse connection portion which connects the two legs, and forms a distal end of the sub-assembly consisting of the plunger rod 9, the rod 15, the second resilient member 13 and the U-bracket 17.

The second resilient member 13 is furthermore configured to bias the U-bracket distally, so that when the plunger rod 9 is released from its axially locked position and moved forward in the proximal direction during medicament administration, as will be described below, the U-bracket 17 is released and thrown backwards in the distal direction, causing auditory feedback when impacting with the end member 19.

The tubular member 11 has radially flexible arms 11a, of which one is shown in FIG. 2, which in an initial rotational position of the movable sleeve 6, are pressed radially inwards by the inner walls of the movable sleeve 6. The plunger rod 9 has an outer surface provided with recesses 9a, of which only one is shown in FIG. 2. Each radially flexible arm 11a is configured to engage with a respective recess 9a when the radially flexible arms 11a are pressed radially inwards by the movable sleeve 6, in particular by the inner walls thereof. In this manner, the plunger rod 9 is maintained in an axially fixed position as long as the movable sleeve 6 is in its initial rotational position, i.e. its position prior to movement of the delivery member cover 5 from the extended, or first, position, towards the retracted, or second, position, which causes rotation of the movable sleeve 6.

The movable sleeve 6 has an inner surface provided with recesses, not shown in FIG. 2. When the movable sleeve 6 is rotated, these recesses align with the radially flexible arms 11a, allowing the radially flexible arms 11a to flex radially outwards, which up until this moment have been pressed radially inwards by the inner walls of the movable sleeve 6, towards their default position. The radially flexible arms 11a thus disengage from the recesses 9a. The plunger rod 9 is hence released from its axially fixed position, and is, due to it being biased in the proximal direction by the second resilient member 13 moved in the proximal direction, causing medicament expulsion as it moves proximally inside the medicament container 21.

Figure 3:
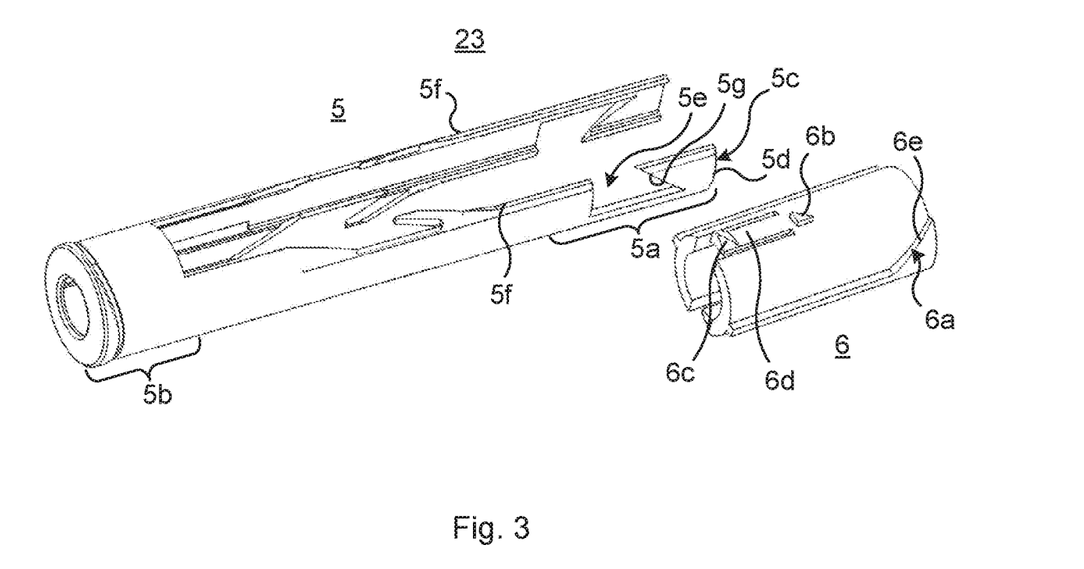
FIG. 3 shows a first example of an administration mechanism for a medicament delivery device.

FIG. 3 shows the delivery member cover 5 and the movable sleeve 6. The delivery member cover 5 and the movable sleeve 6 form or form part of, an administration mechanism 23.

The delivery member cover 5 has means for preventing rotation relative to the housing 3. Such means may for example be axial ribs or grooves arranged on the outer surface of the delivery member cover 5, configured to be engaged with corresponding grooves or ribs, respectively, of the inner surface of the housing 3. Alternatively, the means may be arranged on the inner surface of the delivery member cover 5, configured to engage with an inner structure of the housing 3, for example a medicament container holder.

The movable sleeve 6 may be configured to be axially fixed relative to the housing 3, or it may be configured to be essentially axially fixed relative to the housing 3. In the latter case, there may be a play present which allows for a certain small axial movement of the movable sleeve 6 relative to the housing 3. The small axial movement, especially during the activation of the medicament delivery device, may be advantageous because it will reduce or minimize the risk of jamming or negatively affecting the movement of the movable sleeve 6 due to tolerance factors or friction between components.

The delivery member cover 5 has a distal end portion 5a, and a proximal end portion 5b. The proximal end portion 5b has a generally tubular shape, and the distal end portion 5a has two legs 5f. The delivery member cover 5 is configured to receive the movable sleeve 6. In particular, the movable sleeve 6 is configured to be arranged between the two legs 5f.

The distal end portion 5a of the delivery member cover 5, in particular each leg 5f, has an end face 5c defining a respective guide surface 5d. The movable sleeve 6 has a radially outwards extending first follower structure 6a. The radially outwards extending first follower structure 6a has a follower surface 6e. It is to be noted that there may be two radially outwards extending first follower structures 6a, each being configured to cooperate with a respective guide surface 5*d*. For the purpose of simplification, only one guide surface 5*d* and one radially outwards extending first follower structure 6*a* will be discussed in the following.

The guide surface 5*d* and the radially outwards extending first follower structure 6*a* are configured to cooperate when the delivery member cover 5 is moved from the first position relative to the movable sleeve 6 towards the second position. According to the present example, the follower surface 6*e* of the radially outwards extending first follower structure is an oblique surface in the axial direction, configured to cooperate with the guide surface 5*d* when the delivery member cover 5 is moved from the first position towards the second position relative to the movable sleeve 6.

The movable sleeve 6 has a radially outwards extending second follower structure 6*b*. The distal end portion 5*a*, in particular each leg 5*f*, furthermore has a cut-out 5*e* which has an open end in the proximal direction. The cut-out 5*e* is configured to receive the radially outwards extending second follower structure 6*b* when the movable sleeve 6 is rotated, i.e. while the radially outwards extending first follower structure 6*a* and the guide surface 5*d* cooperate. Furthermore, the cut-out 5*e* has a wall 5*g*, according to the present example an inclined distal end wall, configured to cooperate with the radially outwards extending second follower structure 6*b* when the cut-out 5*e* has received the radially outwards extending second follower structure 6*b* and the delivery member cover 5 is released and returned towards the first position, causing further rotation of the movable sleeve 6. Hereto, the movable sleeve 6 is subjected to a first rotational motion when the delivery member cover 5 is moved from the first position to the second position and to a second rotational motion when the delivery member cover is moved from the second position back towards the first position. This may be advantageous in that a sensor may be utilised to detect both the commencement of medicament administration by detecting the first rotational motion, and to detect that medicament administration has finalized by detecting the second rotational motion.

The radially outwards extending second follower structure 6*b* may have a triangular shape, with one edge of the triangle forming a distal end point of the radially outwards extending second follower structure 6*b*. The radially outwards extending second follower structure 6*b* may thus follow the inclined distal end wall of the cut-out 5*e* such that the radially outwards extending second follower structure 6*b* is fully received in the triangular space formed between the inclined distal end wall and the adjacent axial wall of the cut-out 5*e* when the delivery member cover 5 has returned to the first position.

The movable sleeve 6 may also have a lock structure 6*c*, extending radially outwards, configured to lock the delivery member cover S in the first position upon return from the second position. Hereto, according to the example in FIG. 3, the movable sleeve 6 has a proximally extending flexible tongue 6*d* and the lock structure 6*c* is provided at a proximal end portion of the proximally extending flexible tongue 6*d*. The lock structure 6*c* may be an essentially wedge-shaped radially outwards extending protrusion. The lock structure 6*c* may be axially aligned with and proximally arranged from the radially extending second following structure 6*b*. Due to the radial flexibility of the proximally extending flexible tongue 6*d*, the lock structure 6*c* is bent radially inwards when the delivery member cover S is returned from the second position towards the first position, until the cut-out Se allows the lock structure 6*c* to flex radially inwards. The lock structure 6*c* will thus bear against the proximal wall Sg of the cut-out Se, preventing the delivery member cover S from being moved from the first position towards the second position.

Figure 4A:
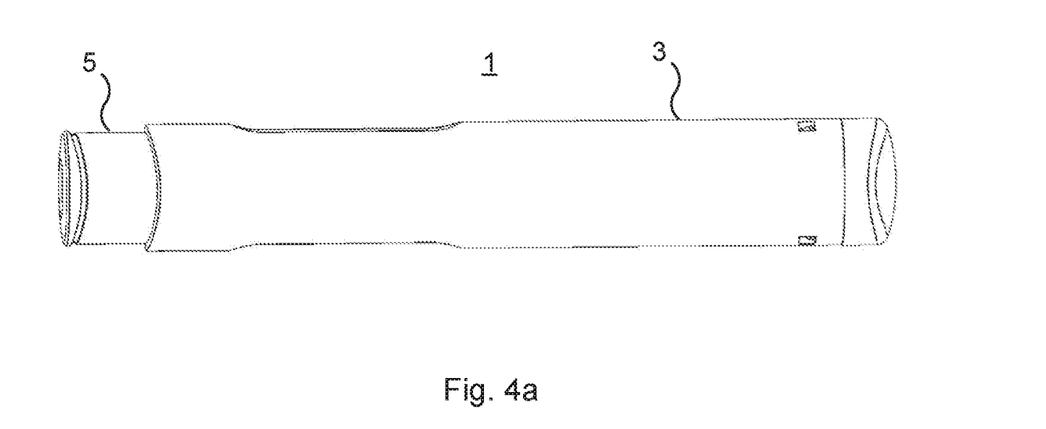
FIG. 4a shows a side view of the medicament delivery device in FIG. 1 prior to activation thereof.

With reference to FIGS. 4*a* to 6*b*, the function of the administration mechanism 23 will be described in more detail. FIG. 4*a* shows a side view of the medicament delivery device 1 with the delivery member cover 5 in the first position relative to the movable sleeve. The delivery member cover 5 is hence in the extended position relative to the housing 3.

Figure 4B:
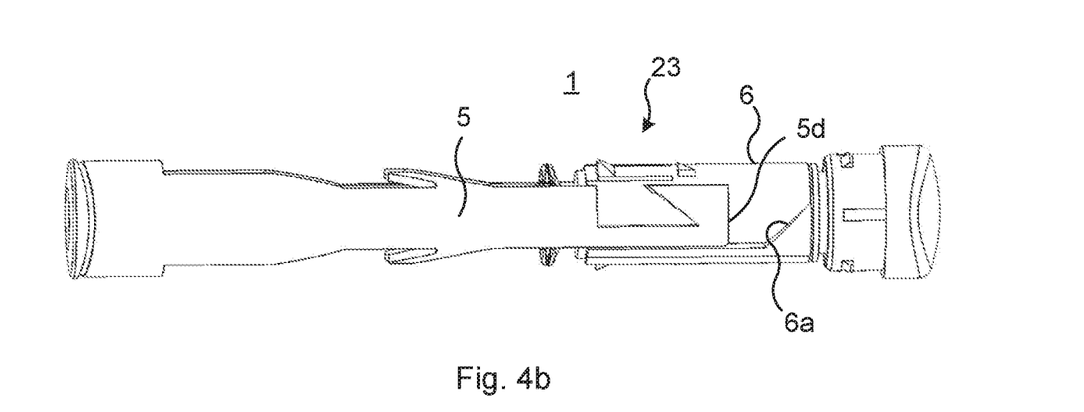
FIG. 4b shows a side view of the medicament delivery device in FIG. 4a with the housing removed to expose interior components.

FIG. 4*b* shows the same state of the medicament delivery device 1 as FIG. 4*a*, but with the housing removed, to expose internal components including the administration mechanism 23. In the state shown in FIG. 4*b*, the guide surface 5*d* has not yet been moved in the distal direction, and thus no cooperation between the guide surface 5*d* and the radially extending first follower structure 6*a* has taken place.

Figure 5A:
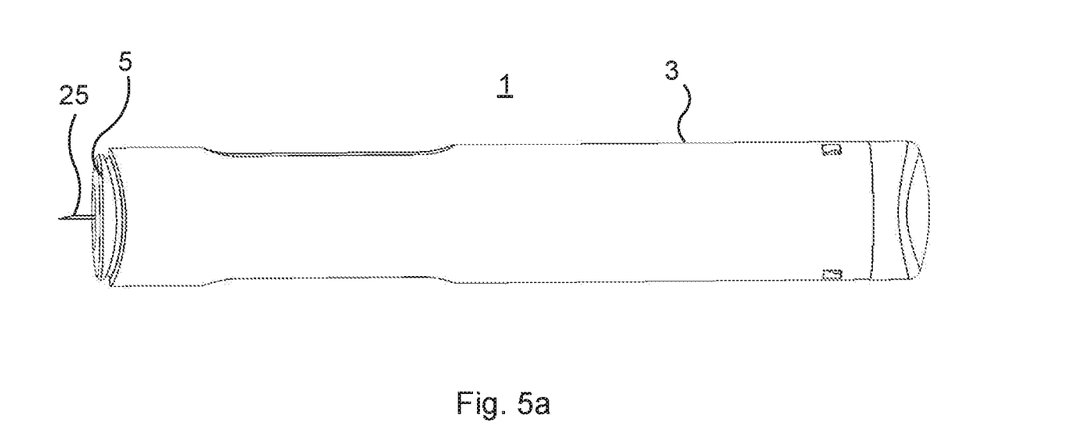
FIG. 5a shows a side view of the medicament delivery device in FIG. 1 during activation thereof.

FIG. 5*a* shows the medicament delivery device 1 in an activated state. The delivery member cover 5 has been displaced distally from the first position relative to the movable sleeve 6 towards the second position, exposing the delivery member 25, in this example a needle. The delivery member cover 5 has hence been moved in the distal direction from the extended position relative to the housing 3 towards the retracted position.

Figure 5B:
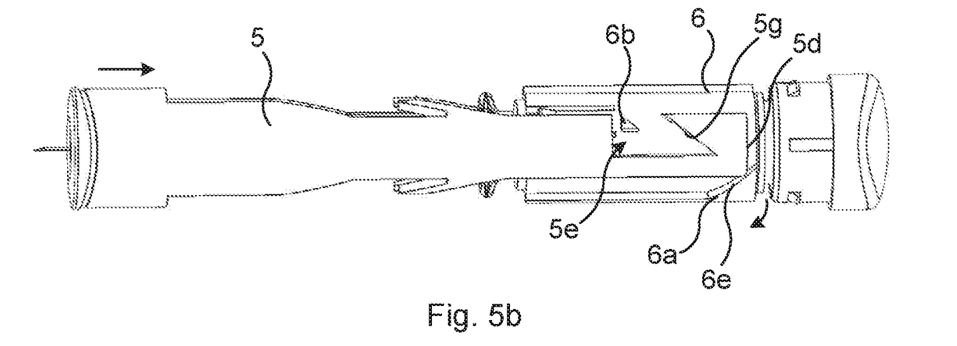
FIG. 5b shows a side view of the medicament delivery device in FIG. 5a with the housing removed to expose interior components.

FIG. 5*b* shows the same state as FIG. 5*a* but with the housing removed. Here, the guide surface 5*d* of the delivery member cover 5 cooperates with the radially outwards extending first follower structure 6*a*, in particular the follower surface 6*e*. As the delivery member cover 5 is moved in the distal direction, the cooperation between the delivery member cover 5 and the movable sleeve 6 causes the movable sleeve 6 to rotate until the end face 5*c* of the delivery member 5 has moved along the entire follower surface 6*e*.

In the situation shown in FIG. 5*b* the radially outwards extending second follower structure 6*b* has moved into the cut-out 5*e* of the delivery member. The radially outwards extending second follower structure 6*b* has however at this point not yet cooperated with the wall 5*g* of the cut-out 5*e*. Moreover, the proximally extending flexible tongue 6*d* is bent radially inwards by the inner surface of the delivery member cover 5.

Figure 6A:
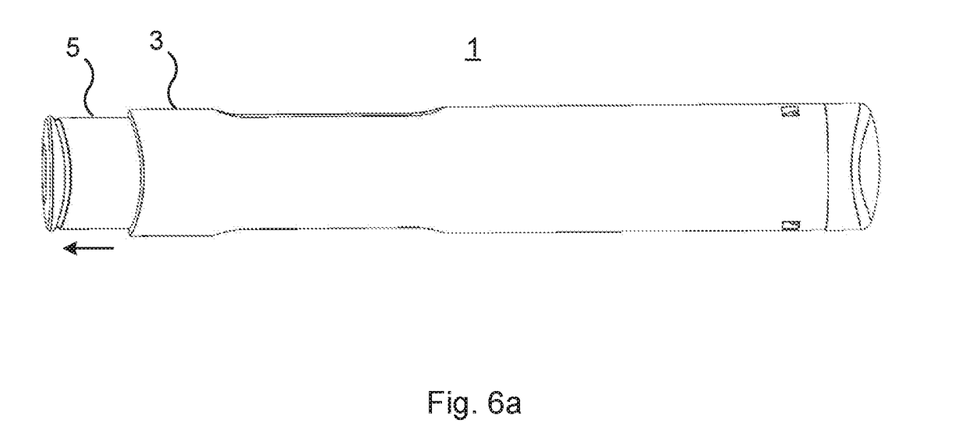
FIG. 6a shows a side view of the medicament delivery device in FIG. 1 after activation thereof.

FIG. 6*a* shows a state of the medicament delivery device 1 in which the delivery member cover 5 has returned from the second position relative to the movable sleeve 6 to the first position, i.e. to the extended position relative to the housing 3.

Figure 6B:
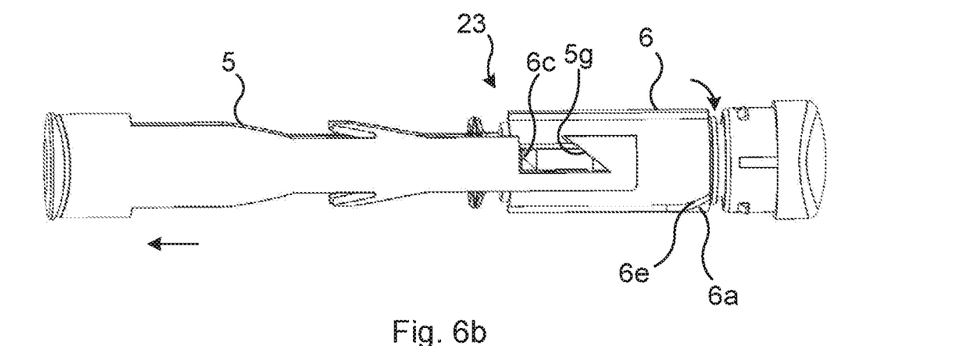
FIG. 6b shows a side view of the medicament delivery device in FIG. 6a with the housing removed to expose interior components.

FIG. 6*b* shows the same state as FIG. 6*a* but with the housing removed. Here, the delivery member cover 5 has been returned, due to its proximal biasing, to the first position relative to the movable sleeve 6. The radially outwards extending second follower structure 6*b* has thus followed the wall 5*g*, which is an inclined distal end wall, of the cut-out 5*e*. This causes additional rotation of the movable sleeve 6, in the same direction as the first rotational motion, when the delivery member cover 5 is returned to the first position. Moreover, the proximally extending flexible tongue 6*d* is moved into the cut-out 5*e*, causing it to flex radially outwards, whereby the lock structure 6*c* extends radially into the cut-out 5*e*, bearing against the proximal wall of the cut-out 5. The lock structure 6*c* is hence snapped into the cut-out 5*e*, preventing the delivery member cover 5 from displacement in the distal direction from the first or extended position.

The delivery member cover may according to one variation have a weakened mechanical structure at each leg, proximally from the cut-outs. This weakened mechanical structure may for example be obtained by providing one or more through-openings aligned with the cut-out. The weakened mechanical structure provides a resilience of the delivery member cover, so that in case the medicament delivery device is dropped onto a rigid surface with the proximal end as the leading edge, the weakened mechanical structure will provide damping of the force so that the impact will be lower on the proximal end wall and the lock structure.

The inclination of the follower surface 6e is a design parameter dependent of the rotation necessary to release the plunger rod 9. The inclination of the wall 5g is dependent of the amount of rotation necessary for detecting further rotation of the movable sleeve, to be able to provide feedback of an end of a drug expulsion.

FIGS. 7a-7e show another example of an administration mechanism for installation in a medicament delivery device such as medicament delivery device 1. Administration mechanism 23' also includes a delivery member cover 5' and a movable sleeve 6', a rotator. Similarly to the first example, linear displacement of the delivery member cover 5' from a first position relative to the movable sleeve 6' to a second position results in cooperation between the delivery member cover 5' and the movable sleeve 6', causing rotation of the movable sleeve 6'.

Like the first example of the administration mechanism, the delivery member cover 5' has a distal end portion 5a' and a proximal end portion 5b'. The proximal end portion 5b' has a generally tubular shape, and the distal end portion 5a' has two legs 5f. The delivery member cover 5' is configured to receive the movable sleeve 6'. The movable sleeve 6' is configured to be arranged between the two legs 5f.

The delivery member cover 5', in particular the distal end portion 5a' has a cut-out 5e' having an open end in the circumferential direction. The cut-out 5e' has an axially extending elongated portion. The delivery member cover 5 furthermore has a through-opening 5i' axially aligned with and distally arranged from the cut-out 5e'.

The delivery member cover 5' furthermore has an end face 5c' which defines a guide surface 5d'. According to the present example, the end face 5c' is a slanting or oblique with respect to the axial direction of the administration mechanism 23'.

The movable sleeve 6' has a radially outwards extending first follower structure 6a'. According to the present example, the radially outwards extending first follower structure 6a' is a circumferentially extending rib. The guide surface 5d' is configured to cooperate with the radially outwards extending first follower structure 6a' when the delivery member cover 5' is moved from the first position to the second position, causing rotation of the movable sleeve 6'.

The movable sleeve 6' furthermore has a lock structure 6c' extending radially outwards. The lock structure 6c' is provided proximally from the radially outwards extending first follower structure 6a'. The lock structure 6c' is furthermore arranged spaced apart from the radially outwards extending first follower structure 6a' in the circumferential direction. The cut-out 5e' is disposed so relative to the lock structure 6c' that the lock structure 6c' is received by the cut-out 5e' when the movable sleeve 6' is rotated by distal movement of the delivery member cover 5'. Due to the elongated shape of the cut-out 5e' the lock structure 6c' is movable in the cut-out 5e', once received therein, when the delivery member cover 5' is moved axially relative to the movable sleeve 6'.

The movable sleeve 6' furthermore has a proximally extending flexible tongue 6d' which is flexible in the radial direction. The lock structure 6c' is provided on a proximal end portion of the proximally extending flexible tongue 6d'. As previously mentioned, the lock structure 6c' is received by the cut-out 5e' when the movable sleeve 6's is rotated, and the proximally extending flexible tongue 6d' is flexed radially inwards when the delivery member cover 5' is returned towards the first position, causing the lock structure 6c' to move below the inner surface of the delivery member cover 5', until it reaches the distally located through-opening 5i', where it is flexed radially outwards and engages with the through-opening 5i'. The delivery member cover 5' will thus be locked in the first position.

Since the distal end portion 5a' is weakened mechanically by the cut-out 5e', which is disposed proximally of and axially aligned with the through-opening 5i', the distal end portion 5a' functions as a damper in the event that the medicament delivery device in which it installed is dropped and the delivery member cover 5' impacts a rigid surface. The impact will thus be dampened, reducing the risk of the lock structure 6c' disengaging from the through-opening 5i'.

It shall be noted that the movable sleeve 6' operates in the same manner as the movable sleeve 6 concerning interaction with the plunger rod, which is released when the movable sleeve 6' is rotated, and this functionality will therefore not be disclosed any further for the present example.

The operation of the administration mechanism 23' will now be described with reference to FIGS. 7a-7e.

Figure 7A:
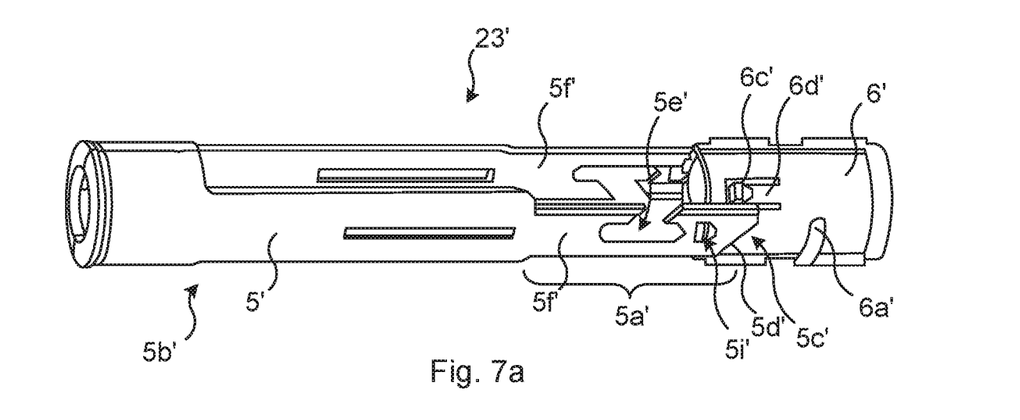
FIG. 7a shows a second example of an administration mechanism for a medicament delivery device, in particular during one stage of use.
Figure 7B:
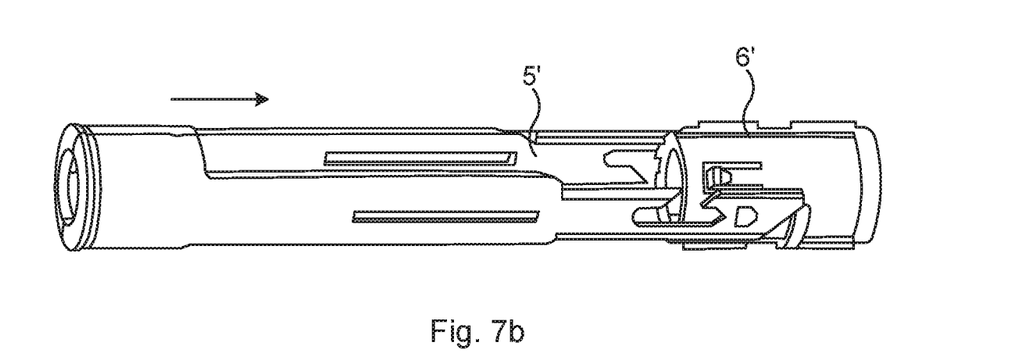
FIG. 7b shows a second example of an administration mechanism for a medicament delivery device, in particular during one stage of use.
Figure 7C:
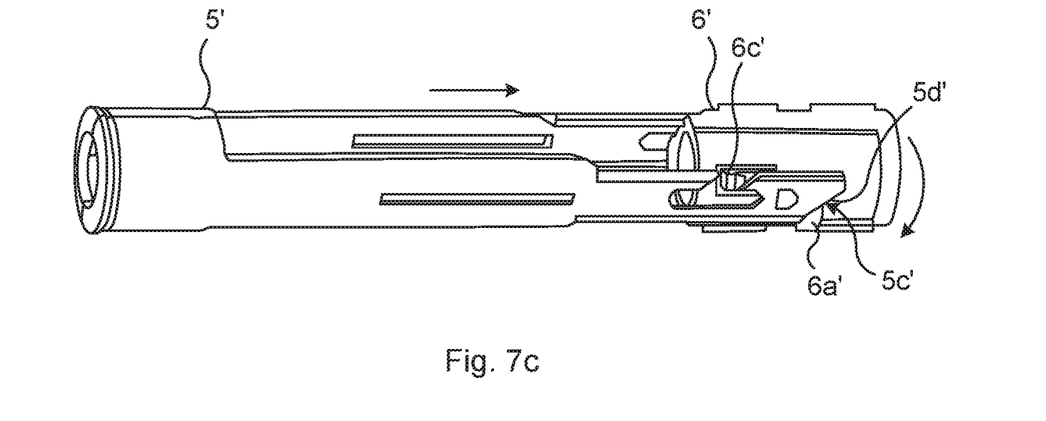
FIG. 7c shows a second example of an administration mechanism for a medicament delivery device, in particular during one stage of use.

In FIG. 7a the delivery member cover 5' is in a first position relative to the movable sleeve 6', corresponding to the extended position relative to the housing, when installed inside a housing. FIG. 7b shows that the delivery member cover 5' is being moved in the distal direction from the first position towards the second position relative to the movable sleeve 6'. In FIG. 7c, the guide surface 5d' of the end face 5c' is cooperating with the radially outwards extending lock structure 6a', causing rotation of the movable sleeve 6' as the delivery member cover 5' is being moved in the distal direction. The lock structure 6c' is being received by the cut-out 5e'.

Figure 7D:
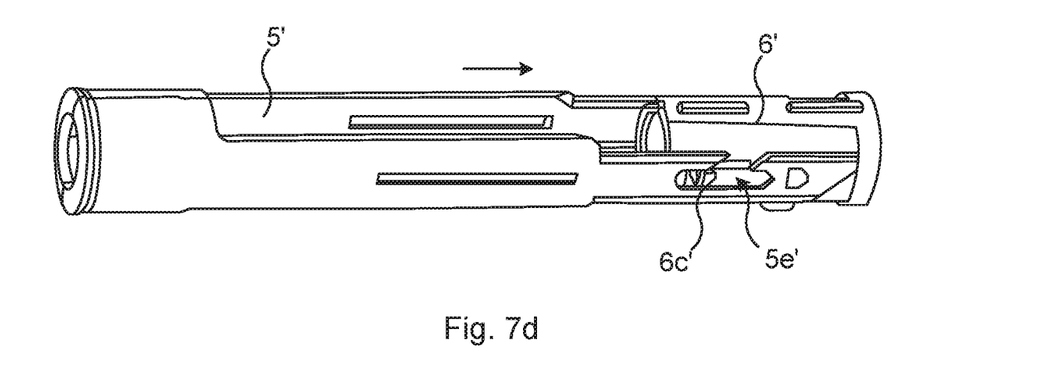
FIG. 7d shows a second example of an administration mechanism for a medicament delivery device, in particular during one stage of use.
Figure 7E:
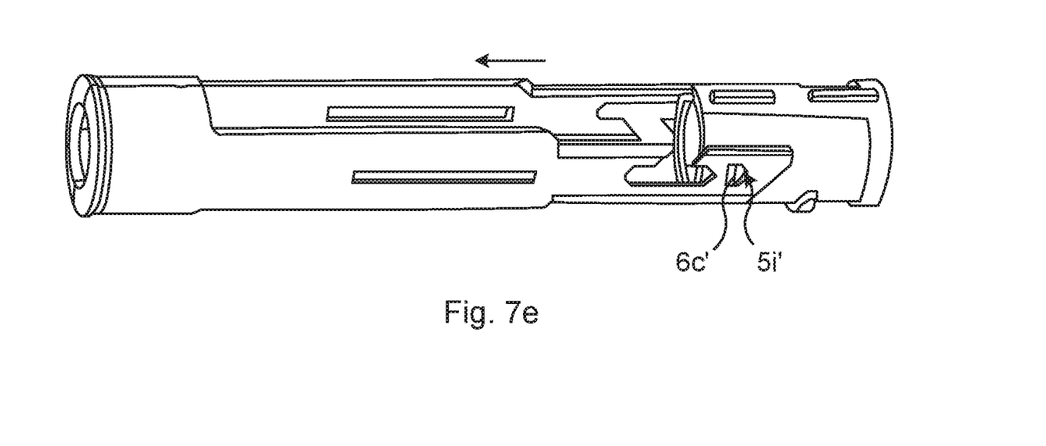
FIG. 7e shows a second example of an administration mechanism for a medicament delivery device, in particular during one stage of use.

In FIG. 7d, the delivery member cover 5' has reached the second position relative to the movable sleeve 6', corresponding to the retracted position relative to the housing, and the lock structure 6c' has been moved to a proximal end of the cut-out 5e'. In FIG. 7e, the delivery member cover 5' has been returned to the first position, and the lock structure 6c' has moved along the cut-out 5e' and snapped into the through-opening 5i'. The delivery member cover 5' is hence prevented from being moved towards the second position.

The inventive concept has mainly been described above with reference to a few examples. However, as is readily appreciated by a person skilled in the art, other embodiments than the ones disclosed above are equally possible within the scope of the inventive concept, as defined by the appended claims.

The invention claimed is:

1. An administration mechanism for a medicament delivery device, comprising:
  a movable sleeve;
  a delivery member cover having a distal end portion configured to receive the movable sleeve, and configured to be linearly displaceable between a first position and a second position relative to the movable sleeve, and
  a first resilient member that biases the delivery member cover towards the first position,
  wherein the distal end portion has an end face defining a guide surface and the movable sleeve has a radially outwards extending first follower structure configured to cooperate with the guide surface when the delivery member cover is moved from the first position towards the second position, causing the movable sleeve to move.

2. The administration mechanism as claimed in claim 1, wherein the movable sleeve comprises a radially outwards extending second follower structure and the distal end portion of the delivery member cover has a cut-out configured to receive the radially outwards extending second follower structure, wherein the radially outwards extending second follower structure is configured to cooperate with a wall of the cut-out, causing rotation of the movable sleeve when the delivery member cover is moved from the second position towards the first position.

3. The administration mechanism as claimed in claim 2, wherein the radially outwards extending second follower structure has a triangular shape and the wall of the cut-out is a slanting surface.

4. The administration mechanism as claimed in claim 2, wherein the movable sleeve has a lock structure configured be received by the cut-out, and configured to prevent movement of the delivery member cover when returned to the first position from the second position.

5. The administration mechanism of claim 1, wherein the radially outwards extending first follower structure has an oblique surface configured to cooperate with the guide surface.

6. The administration mechanism as claimed in claim 1, wherein the radially outwards extending first follower structure is a circumferentially extending rib.

7. The administration mechanism as claimed in claim 1, wherein the movable sleeve has a lock structure that is received in a delivery member cover cut-out when the movable sleeve is rotated by the delivery member cover.

8. The administration mechanism as claimed in claim 7, wherein the cut-out has an axially extending elongated portion configured to allow linear displacement of the delivery member cover relative to the lock structure when the lock structure is arranged in the cut-out.

9. The administration mechanism as claimed in claim 7, wherein the lock structure is flexible radially inwards and the delivery member cover has a through-opening configured to receive the lock structure when the delivery member cover is returned from the second position to the first position.

10. The administration mechanism as claimed in claim 9, wherein the through-opening is arranged distally from and axially aligned with the axially extending elongated portion of a cut-out.

11. The administration mechanism as claimed in claim 9, wherein the lock structure and the through-opening form a snap lock function.

12. The administration mechanism of claim 7, wherein the lock structure is arranged proximally relative to the radially outwards extending first follower structure.

13. The administration mechanism of claim 1, wherein the guide surface is a cam surface.

14. A medicament delivery device comprising:
a housing having a proximal opening, and
an administration mechanism, comprising:
a movable sleeve; and
a delivery member cover having a distal end portion configured to receive the movable sleeve, and configured to be linearly displaceable between a first position and a second position relative to the movable sleeve, and
a first resilient member that biases the delivery member cover towards the first position,
wherein the distal end portion has an end face defining a guide surface and the movable sleeve has a radially outwards extending first follower structure configured to cooperate with the guide surface when the delivery member cover is moved from the first position towards the second position, causing the movable sleeve to move, wherein the administration mechanism is configured to be received within the housing.

15. The medicament delivery device as claimed in claim 14, wherein in the first position the delivery member cover is configured to extend from the proximal opening, and wherein the delivery member cover is configured to be rotationally locked relative to the housing.

16. The medicament delivery device of claim 15 wherein the distal end portion comprises a cut-out and a through opening.

17. The medicament delivery device of claim 16 wherein the moveable sleeve comprises a lock structure.

18. The medicament delivery device of claim 17 where the lock structure first engages the cut-out prior to engagement with the through opening.

19. The medicament delivery device of claim 15 further comprising a hollow plunger rod containing a resilient member.

* * * * *